US00PP10638P

United States Patent [19]

Olesen et al.

[11] Patent Number: Plant 10,638

[45] Date of Patent: Oct. 13, 1998

[54] SHRUB ROSE PLANT NAMED 'POULUSA'

[75] Inventors: Pernille Olesen; Mogens Olesen, both of Fredensborg, Denmark

[73] Assignee: Weeks Wholesale Rose Grower, Inc., Upland, Calif.

[21] Appl. No.: 960,784

[22] Filed: Oct. 30, 1997

[51] Int. Cl.[6] ..... A01H 5/00

[52] U.S. Cl. ..... Plt./1

[58] Field of Search ..... Plt./1, 22, 26

*Primary Examiner*—Howard J. Locker
*Attorney, Agent, or Firm*—Christie, Parker & Hale, LLP

[57] ABSTRACT

A new variety of Shrub rose suitable for garden decoration, having flowers of very pale pink coloration.

1 Drawing Sheet

BACKGROUND OF THE INVENTION

This invention relates to a new and distinct variety of Hybrid Shrub Rose. The varietal denomination of the new variety is 'Poulsusa'. Its seed parent is an undistributed seedling and as its pollen parent is the variety known as 'Poulskov' (U.S. Plant Pat. No. 9,062).

SUMMARY OF THE INVENTION

Among the features which distinguish the new variety from other presently available and known commercial rose cultivars are the following combination of characteristics: Its pale pink flower coloration, its low compact rounded habit and very full branching and its abundant semi-glossy deep green foliage. The plant is a bushy compact plant, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'Poulusa' may be asexually propagated by cuttings, budding or grafting.

COMPARISON WITH PARENTS

The new rose may be distinguished from its seed parent, an undistributed seedling, by the following combination of characteristics: whereas 'Poulusa' bears double flowers of pale pink coloration, the seed parent bears flowers of significantly darker pink coloration and semi-double petalage. The seed parent has foliage with a very glossy finish, whereas 'Poulusa' has foliage of a significantly less glossy finish.

The new variety may be distinguished from its pollen parent, 'Poulskov' by the following combination of characteristics: whereas 'Poulusa' bears flowers of a pale pink coloration, 'Poulskov' bears flowers of a significantly darker pink coloration. The pollen parent bears very double flowers of about 48 to about 62 petals, whereas the new rose bears flowers of significantly lower petalage (about 27 to about 42).

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in th month of October. Phenotypic expression may vary with environmental, cultural and climatic conditions, as well as differences in conditions of light and soil.

Flower

The new variety bears its flowers sometimes singly, usually in clusters of three to four or more per stem. Flowers are borne in irregular somewhat rounded clusters on normal short to medium stems (about 10 to about 16 cms.). Outdoors, the plant blooms very abundantly and nearly continuously during the growing season. The flowers have a slight apple-like to spicy fragrance.

Bud

The peduncle is about 4 to about 5.5 l cms. in length, of average caliper, and usually erect. It is moderately smooth, with some stipitate glands. Peduncle color is between 144A and 138A.

Before the calyx breaks, the bud is about 1.3 to about 1.6 cms. in diameter at the widest point, about 1.8 to about 2.2 cms. in length, and pointed to ovoid in shape. The surface of the bud is moderately smooth and bears some stipitate glands, usually with slender entire foliaceous parts extending beyond the tip of the bud equal to ¾ or more of its length. Bud color is between 144A and 138A.

The inner surface of the sepals is covered with fine wooly tomentum; sepal margins are lined with some stipitate glands and hairs.

As the petals open (after the calyx breaks), the bud is about 1.5 to 2 cms. in diameter at the widest point, about 2 to about 2.5 cms. in length, and pointed to ovoid in form. The color of the under surfaces of the newly opened petals is between 49C and 36C. At the point where the petal attaches, there is a moderately small zone near 2C. The color of the upper surfaces of the newly opened petals is between 49D and 36D. At the point where the petal attaches, there is a small zone of near 2C.

Bloom

When fully open, the bloom ranges from about 7.5 to about 9 cms. in diameter. Petalage is double with about 27 to 42 petals and about 3 to 8 or more petaloids arranged irregularly. When partially open, the bloom form is somewhat cupped to high centered, and the petals are spiraled to cupped with petal edges slightly reflexed outward. When fully open, the bloom form is somewhat more flat to cupped, and the petals are somewhat cupped to undulated with petal edges very slightly reflexed outward.

Petals the subtance of the petals is somewhat heavy and of medium thickness, with upper surfaces somewhat satiny and under surfaces slightly shiny to satiny. The outer petals are nearly round to very broadly obovate in shape with apices usually moderately rounded but sometimes slightly mucronate. The inner petals are more narrowly obovate in shape with apices usually moderately rounded but sometimes slightly mucronate.

Newly Opened Flower

The under and upper surface of the outer, intermediate and inner petals is between 49D and 36D. At the point where the petal attaches, there is a moderately small zone of near 2C.

The general tonality of the newly opened flower is between 49D and 36D.

Three Day Old Flower

The under and upper surface of the outer and inner petals is between 36D and 155D. At the point where the petal attaches, there is no zone of different coloration.

The general tonality of the three day old flower is between 36D and 155D.

The petals of spent blooms usually drop off cleanly.

In October in Upland, Calif., blooms on the bush growing outdoors generally last about four to five or more days. Cut roses from plants grown outdoors and kept at normal indoor living temperatures generally last from four to five or more days.

Male Reproductive Organs

Stamens are average to many in number (approximately 130) and are arranged regularly about the pistil. the filaments are of medium to long length, most with anthers. The anthers are moderately small to medium size for the class and all open approximately at the same time. Anther color is between 15C and 23C when immature and near 165B at maturity. Pollen is moderately abundant and near 13D in color.

Female Reproductive Organs

Pistils vary in number (approximately 72). The styles are moderately uneven, short to average in length, moderately thin in caliper, and somewhat bunched. Stigma color is between 11C and 16C. Style color is near 2D. Ovaries are usually all enclosed in the calyx.

Hips are of somewhat short length, nearly round to globular in form and near 25B in color when ripe. The hip surface is very smooth with somewhat thick fleshy walls. The sepals fall away soon. Seeds vary in number (approximately 8 to 14) and are usually moderately small in size.

Foliage

The compound leaves are usually comprised of three to five leaflets and are borne abundantly. The leaves are about 7 to about 10 cms. in length and about 5.5 to about 8.5 cms. in width at the widest point, moderately heavy in texture, and semi-glossy in finish. The leaflets are about 2.5 to about 6 cms. in length and about 1.5 to about 3.5 cms. in width at the widest point, oval in shape with moderately acute apices and have somewhat round to acute bases. Their margins are usually simply serrate.

The upper surface of the mature leaf is betwwen 137A and 139A. The under surface of the mature leaf is between 137C and 139C. The upper surface of the young leaf is beween 147A and 139A, usually heavily suffused with between 183A and 178B. The under surface of the young leaf is between 147B and 139C, moderately heavily suffused with between 183A and 178B.

The rachis is somewhat light to average in caliper and moderately smooth. The upper side is moderately grooved with few hairs and stipitate glands on the edges of the grooves. The under side of the rachis is very smooth with few hairs and stipitate glands.

The stipules are average to long in length with somewhat narrow moderately short straight points that usually turn out at an angle of more than 45 degrees.

The plant displays an average degree of resistance to powdery mildew as compared to other commerical varieties grown under comparable conditions in Upland, Calif.

Growth

The plant has a bushy compact moderately low habit (about 65 to about 80 cms. in height and about 70 to about 85 cms. spread at the widest point), with very full branching. It displays very vigorous growht and the canes are of somewhat light to medium caliper for the class.

The color of the major stems is between 147B and 146C. They bear very few large prickles which are about 0.7 to about 0.8 cms in length. The large prickles are almost straight with a somewhat short length moderately broad to nearly rounded base; prickle color is near 166C. The major stem bears very few small prickles of similar shape and coloration and which are about 0.5 to about 0.6 cms in length.

The color of the branches is between 137B and 144A. They bear very few large prickles which are of similar size and shape to the large prickles on the major stems. The branches bear very few small prickles whtich are of similar size and shape to the small prickles on the major stems. Prickle color on the branches is between 144B and 160C.

The color of the new shoots is between 144A and 146B often lightly suffused with between 183A and 178B. They bear very few large prickles which are of similar size and shape to the large prickles on the major stems. The new shoots bear very few small prickles which are of similar size and shape to the small prickles on the major stems. Prickle color on the new shoots is near 144A often moderately suffused with between 183A and 178B.

We claim:

1. A new and distinct variety of Shrub rose plant substantially as described and illustrated herein.

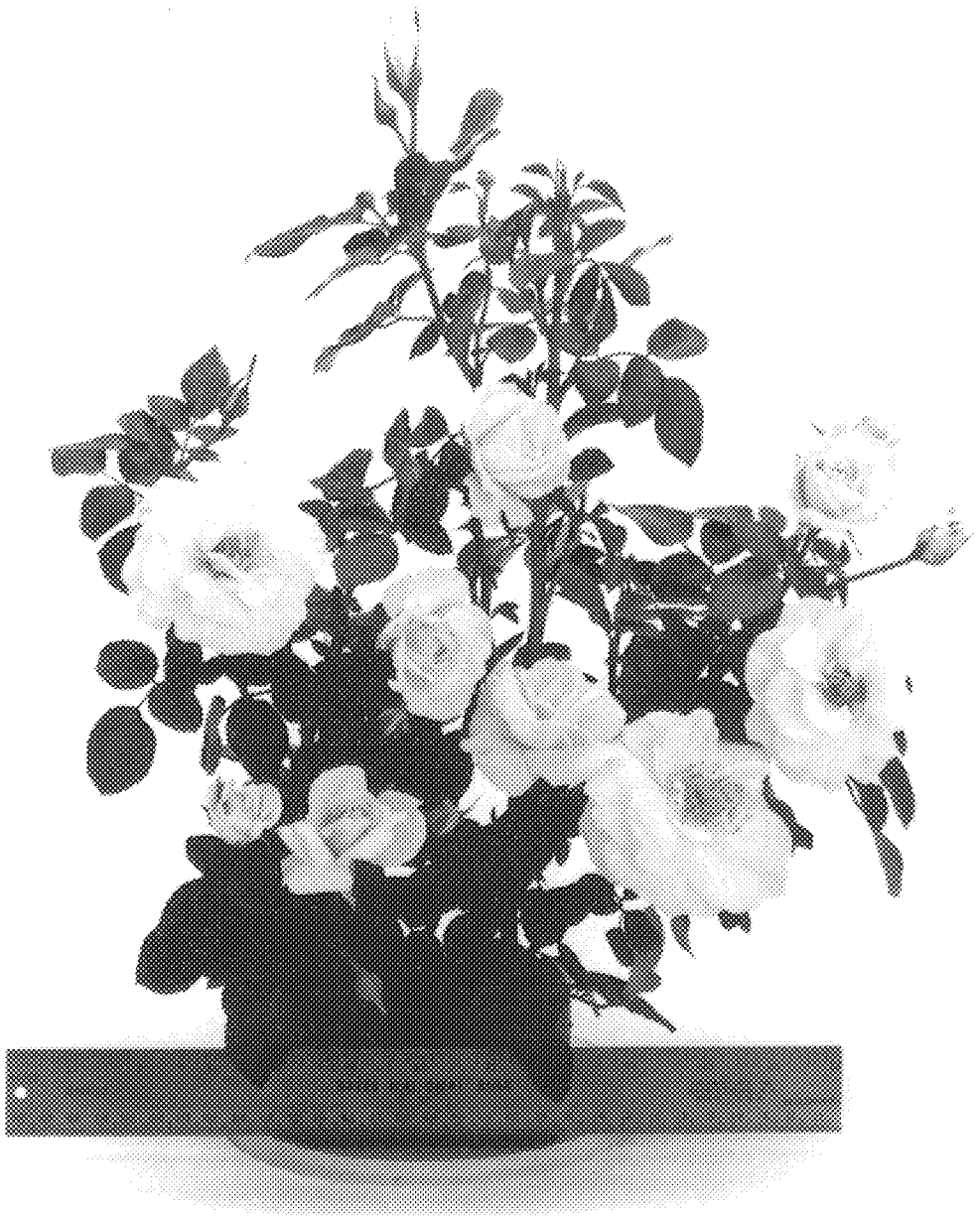

* * * * *